(12) United States Patent
Ullrich

(10) Patent No.: US 8,773,247 B2
(45) Date of Patent: Jul. 8, 2014

(54) HAPTIC FEEDBACK DEVICE USING STANDING WAVES

(75) Inventor: Christopher J. Ullrich, Ventura, CA (US)

(73) Assignee: Immersion Corporation, San Jose, CA (US)

( * ) Notice: Subject to any disclaimer, the term of this patent is extended or adjusted under 35 U.S.C. 154(b) by 715 days.

(21) Appl. No.: 12/638,222

(22) Filed: Dec. 15, 2009

(65) Prior Publication Data

US 2011/0140870 A1 Jun. 16, 2011

(51) Int. Cl.
*H04B 3/36* (2006.01)

(52) U.S. Cl.
USPC ......................... 340/407.1; 340/4.1

(58) Field of Classification Search
USPC .................. 340/407.1, 407.2, 573.1, 4.1
See application file for complete search history.

(56) References Cited

U.S. PATENT DOCUMENTS

| | | | | |
|---|---|---|---|---|
| 5,222,895 | A * | 6/1993 | Fricke | 434/113 |
| 6,384,715 | B1 * | 5/2002 | Potter | 340/407.1 |
| 7,176,895 | B2 * | 2/2007 | Harif | 345/169 |
| 2004/0025624 | A1 * | 2/2004 | Kreuzer | 74/552 |
| 2007/0109104 | A1 * | 5/2007 | Altan et al. | 340/407.1 |
| 2008/0287167 | A1 * | 11/2008 | Caine | 455/575.1 |
| 2009/0181724 | A1 * | 7/2009 | Pettersson | 455/566 |
| 2010/0141407 | A1 * | 6/2010 | Heubel et al. | 340/407.1 |

* cited by examiner

*Primary Examiner* — Brent Swarthout
(74) *Attorney, Agent, or Firm* — Pillsbury Winthrop Shaw Pittman LLP

(57) ABSTRACT

Haptic output devices and related systems and methods are described in the present disclosure. In various implementations, a haptic output device includes a reservoir filled with a liquid. At least one side of the reservoir includes a flexible membrane. The haptic output device also includes a first actuator in physical contact with the reservoir and configured to impart pressure waves to the liquid. The pressure waves interact with the flexible membrane to supply a haptic effect to a user.

26 Claims, 2 Drawing Sheets

HAPTIC FEEDBACK DEVICE USING STANDING WAVES

TECHNICAL FIELD

The present disclosure generally relates to providing haptic feedback and, more particularly, to haptic output devices that create standing waves in a liquid medium.

BACKGROUND

Electronic device manufacturers strive to produce a rich interface for users. Conventional electronic devices often provide visual and/or auditory feedback to communicate information to users. In some cases, kinesthetic feedback (such as active and resistive force feedback) and/or tactile feedback (such as vibration, texture, and heat) may also be provided to the user to enhance the user experience. Generally speaking, kinesthetic feedback and tactile feedback are collectively known as "haptic feedback" or "haptic effects." Haptic feedback may be useful for providing cues to alert the user of specific events or to provide realistic feedback sensations to create a greater sensory experience. Haptic feedback can be used with common electronic devices and even devices used for creating a simulated or virtual environment.

In order to generate haptic effects, different types of haptic actuators can be utilized. Examples of known haptic actuators include electromagnetic actuators, such as an Eccentric Rotating Mass (ERM) in which an eccentric mass is moved by a motor, a Linear Resonant Actuator (LRA) in which a mass attached to a spring is driven back and forth, "smart materials" such as piezoelectric materials, electro-active polymers, or shape memory alloys, etc. Many of these actuators and the devices with which they interact typically have resonant frequencies, which can be built in or dynamically determined. Drive signals can be applied to the actuators to generate the haptic effects effectively and efficiently.

SUMMARY

The present disclosure describes systems, electronic devices, and input/output devices for providing haptic feedback to a user. In some implementations, a haptic output device includes a reservoir filled with a liquid, where at least one side of the reservoir includes a flexible membrane. The haptic output device may also include a first actuator and/or a second actuator, each in physical contact with the reservoir. Regarding embodiments comprising two actuators, the first actuator and second actuator are positioned a fixed distance apart from each other on opposite ends of the reservoir. Furthermore, the first actuator and/or second actuator are configured to be driven so as to impart pressure waves on the liquid.

Various implementations described in the present disclosure may include additional features and advantages, which may not necessarily be expressly disclosed herein but will be apparent to one of ordinary skill in the art upon examination of the following detailed description and accompanying drawings. It is intended that these features and advantages be included within the present disclosure.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

DETAILED DESCRIPTION

The present disclosure describes embodiments of haptic output devices, which provide haptic effects on a user. In particular, various implementations of the haptic output devices described herein may be incorporated into an article of clothing, garment, wrap, pad, patch, or other material that may be worn by the user or attached in some manner to or in contact with the user's body. In this respect, the haptic output device can be configured to provide haptic effects to the user at specific locations on the user's body where the wearable material touches the user's skin. For example, various implementations of the haptic output devices described herein may be incorporated within a shirt to provide haptic effects on the user's arms, back, and/or shoulders. Thus, when used in clothing or other wearable material, the haptic output devices may be used to provide socio-affective sensations for the user.

Also, various implementations of the haptic output devices may be used in environments where visual and/or auditory feedback may not be a viable means for communication. For example, the haptic output devices may be useful in harsh environments, such as during a rescue mission by a group of firefighters. In a rescue situation within a burning building, for instance, the firefighters might not be able to communicate using visual or auditory signals. Thus, haptic effects may prove to be a more advantageous means of communication between firefighters in this situation. For example, if a radio alert is given to a team of firefighters to pull out, haptic effects in the form of a tap on the shoulder or squeeze of the arm can be administered in order to communicate commands effectively.

Various implementations of haptic output devices may also be used in stealth or secretive environments, where only the recipient of the haptic effect is intended to receive a specific communication. The application in this type of environment may include use by policemen or soldiers in the field, for enabling communication without visual and/or auditory feedback, which may otherwise compromise the recipient's position. Also, this type of haptic effect could be used in athletics for communicating signals between players and/or coaches without the visual or audible interception of the signal by members of another team.

In various implementations, the haptic output devices may be incorporated within user devices, such as electronic handheld devices, for providing a rich sensory experience for the user. Although various implementations of the invention are described as haptic output devices incorporated into certain devices or in certain environments, the haptic output devices may be used in other devices and/or environments. Other features and advantages may become apparent to one of ordinary skill in the art upon reading and understanding the general principles of the present disclosure.

Figure 1:
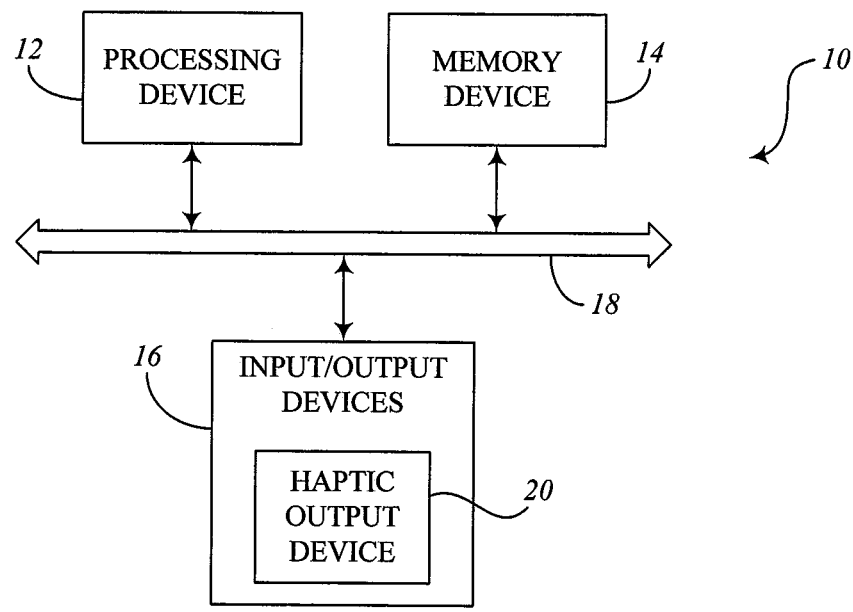
FIG. 1 is a block diagram illustrating an electronic device according to various implementations of the invention.

FIG. 1 is a block diagram showing an electronic device 10 in accordance with various implementations of the invention. More particularly, electronic device 10 includes a processing device 12, a memory device 14, and/or various input/output devices 16, which are interconnected via a bus 18. Furthermore, input/output devices 16 may include a haptic output device 20.

Haptic output device 20 is configured to communicate haptic effects to the user that can be tactilely sensed by the user. In some implementations of the invention, haptic output device 20 may be incorporated with another output device that can communicate signals directed to the user's sense of touch. In some implementations of the invention, haptic output device 20 may be part of or associated with any suitable human-computer interface, such as a touch screen, touch pad, touch sensitive structure, slide control device, buttons, knobs, or other touchable input/output devices 16. Haptic output device 20 may be configured for physical interaction with a user-controlled device, such as a stylus, finger, etc. In some implementations of the invention, haptic output device 20 may include at least one output device and at least one input device, such as a touch screen. In those implementations, haptic output device 20 might include a visual display and a touch sensitive screen superimposed thereon to receive inputs from a user's finger.

In various implementations of the invention, haptic output device 20 provides haptic feedback to at least a portion of electronic device 10, which can be conveyed to a user in contact with electronic device 10. Particularly, haptic output device 20 can provide haptic effects directly to a user when the user is in contact with the device. In some implementations of the invention, haptic output device 20 may provide indirect haptic effects to the user via a housing of electronic device 10, via any other suitable portion of electronic device 10, or via a wearable material or other object in which haptic output device 20 may be incorporated.

Electronic device 10 may be configured as a computer, electronic handheld device (such as a mobile phone, personal digital assistant (PDA), portable e-mail device, portable Internet access device, calculator, etc.), game controller, or other electronic device. In some implementations of the invention, electronic device 10 may be a portable processing component incorporated into another device or component. For example, electronic device 10 may be incorporated in clothing or other wearable material for providing haptic effects while the user is in contact with the clothing or material.

Processing device 12 may be a general-purpose or specific-purpose processor or microcontroller for managing or controlling the operations and functions of electronic device 10. For example, processing device 12 may be specifically designed as an application-specific integrated circuit ("ASIC") to control output signals to one or more drivers of input/output devices 16 to provide haptic effects. Processing device 12 may be configured to decide, based on predefined factors, what haptic effects are to be played, the order in which the haptic effects are played, and the magnitude, frequency, duration, and/or other parameters of the haptic effects. Processing device 12 can also be configured to provide streaming motor commands that can be used to drive the haptic actuators for creating a particular haptic effect. In some embodiments, processing device 12 may actually include a plurality of processors, each configured to perform certain functions within electronic device 10.

Memory device 14 may include one or more internally fixed storage units, removable storage units, and/or remotely accessible storage units, and may include a tangible storage medium. The various storage units may include any combination of volatile memory and non-volatile memory. The storage units may be configured to store any combination of information, data, instructions, software code, etc. More particularly, the storage devices may include haptic effect profiles, instructions for how the haptic actuation devices of input/output devices 16, e.g., haptic output device 20, are to be driven, or other information for generating haptic effects.

Memory device 14 may be configured to store a program for enabling actuation of haptic output device 20. In some embodiments, the program may be configured to synchronize the actuation of two pressure waves at opposing ends of an actuating device to create standing waves in a liquid medium within the actuating device, as described in more detail below. In some implementations of the invention, the liquid medium is under pressure thereby limiting movement with the actuating device. The actuators may then be used to impose pressure waves on the liquid medium and cause movement of the medium along one axis without causing substantial, if any, movement along another axis. For example, the pressure waves may cause lateral movement and cause little if any longitudinal movement. In addition, the program stored in memory device 14 may also take into account the dimensions of a reservoir designed to contain the medium. This may allow certain wave patterns to be formed in the medium. Actuation algorithms may involve Fourier transforms, calculations of harmonic expansions, or other time and frequency calculations for creating specific wave patterns.

In some implementations of the invention, haptic output device 20 may be the only input/output device 16 of electronic device 10, such as, for example, when using the haptic output device 20 in clothing. In some implementations of the invention, in addition to haptic output device 20, input/output devices 16 may also include specific input mechanisms and output mechanisms. For example, the input mechanisms may include such devices as keyboards, keypads, cursor control devices (e.g., computer mice), or other data entry devices. Output mechanisms may include a computer monitor, virtual reality display device, audio output device, printer, or other peripheral devices. Input/output devices 16 may include mechanisms that are designed not only to receive input from a user, but also provide feedback to the user, such as a touch screen devices. Haptic output device 20 and other input/output devices 16 may include any suitable combination and configuration of buttons, keypads, cursor control devices, touch screen components, stylus-receptive components, or other data entry components. Input/output devices 16 and haptic output device 20 may also include any suitable combination of computer monitors, display screens, touch screen displays, haptic or tactile actuators, haptic effect devices, or other notification devices for providing output to the user.

Figure 2:
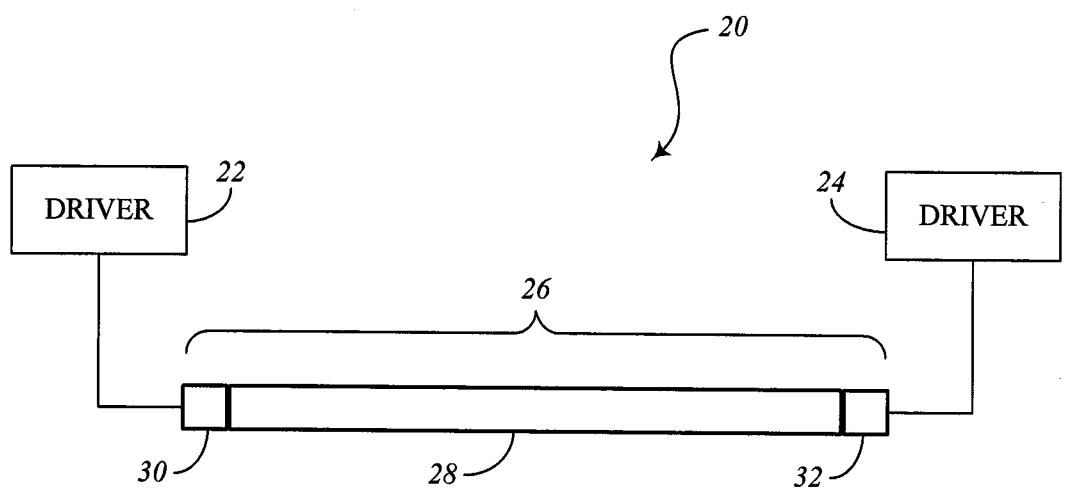
FIG. 2 is a diagram illustrating the haptic output device shown in FIG. 1, according to various implementations of the invention.

FIG. 2 is a block diagram illustrating an embodiment of haptic output device 20 shown in FIG. 1, according to various implementations of the invention. Haptic output device 20 includes a first driver 22, a second driver 24, and an actuating device 26. Actuating device 26 includes a reservoir 28, a first pressure actuator 30 and a second pressure actuator 32. In some implementations of the invention, the first pressure actuator 30 is disposed at one end of reservoir 28 and the second pressure actuator 30 is disposed at the other end of reservoir 28.

Reservoir 28 comprises liquid-tight materials and is configured to be filled with a liquid, such as water, oil, a magneto-rheological liquid, an electro-rheological liquid, or other suitable liquid medium. In some implementations of the invention, reservoir 28 is to be filled completely or almost completely with the liquid. In some implementations, the liquid inside reservoir 28 is pressurized in order that the pressure waves can be transmitted through the liquid. In order for pressure waves to be transmitted adequately through the liquid, the liquid should be substantially incompressible and should have a substantially linear stress-to-strain response within the actuation pressure range. Furthermore, reservoir 28 includes at least one side having a flexible membrane that can deform to the shapes or patterns of pressure waves that are transmitted through the liquid within reservoir 28 via at least one pressure actuator.

In some implementations of the invention where the fluid in reservoir 28 includes suspensions of electrical and/or magnetic particles, for example, as with various electro-rheological and magneto-rheological fluids, the reservoir 28 may be augmented with passive and/or active electromagnetic field generators such as magnets, electromagnets, current carrying wires, or other electromagnetic field generators. These electromagnetic field generators may be used to act upon the electrical and/or magnetic particles in such a way as to create controllable sub-regions within the reservoir 28. The particles can be controlled by the electromagnetic field generators for the purpose of further localizing the pressure waves, normalizing the geometry of the reservoir 28, dynamically adjusting the fluid properties, and other purposes. This may result in enhanced performance by the haptic output device 20.

In some implementations of the invention, first pressure actuator 30 and second pressure actuator 32 may be configured on opposite ends of reservoir 28 and may be supported at a fixed distance away from each other. The pressure actuators 30, 32 are placed in contact with the ends of reservoir 28 in order to be able to transmit vibrations to the liquid within reservoir 28. First pressure actuator 30 and second pressure actuator 32 may include piezoelectric actuators, voice coils, or any other types of actuators. In some implementations of the invention, first pressure actuator 30 and second pressure actuator 32 are configured to operate within a frequency range from about 0 Hz (DC) to about 2 kHz, though other frequency ranges may be used.

First pressure actuator 30 and second pressure actuator 32 can impart pressure waves to the liquid medium of reservoir 28 to create cumulative interference effects along the length of the deformable membrane of reservoir 28. Driver 22 and driver 24 can be controlled by synchronized signals to create various wave patterns. For example, pressure actuators 30 and 32 can be driven to create standing waves, peaks, troughs, rippling waves, or other waveforms, by regulating the pressure wave frequencies and harmonics. Also, the length, width, and height of reservoir 28 may be considered to produce various pressure wave patterns. In some embodiments, the reservoir may also include sensing elements that can be used to estimate the configuration of the reservoir itself, which could then be used to refine the control signals sent to the actuators.

Although FIG. 2 defines haptic output device 20 having two actuators on opposite ends of reservoir 28, haptic output device 20 may be configured in other implementations with a single driver and a single actuator. In these implementations, the driver may be configured to drive the actuator with a specific wave pattern. Because the waves reflect off the opposite end of the reservoir in this case, the reflections may be used with pressure waves driven by a single actuator to generate various wave patterns along the length of reservoir 28.

In implementations with a single pressure actuator, a rigid surface may replace the second pressure actuator 32 to enable reflections of the pressure waves. In some implementations, a flexible membrane may replace the second pressure actuator 32. In various implementations of the invention, a sensor configured to sense the pressure within reservoir 28 may be used. Pressure data sensed by the sensor can be fed back to driver 22 to form a feedback loop in order to properly control the output waves. Based on the sensed waves, the driver 22 can adjust the output signal to compensate for various environmental conditions.

Figure 3A:
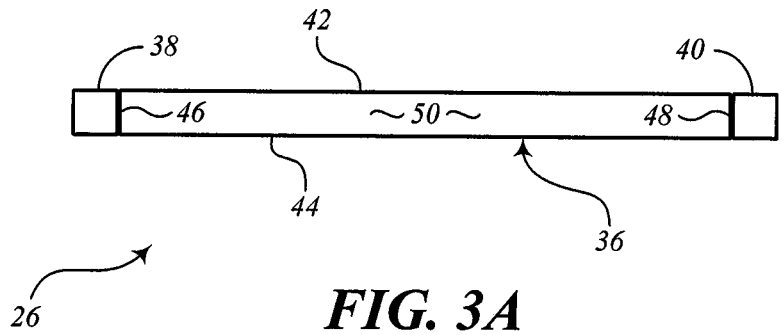
FIG. 3A is a diagram illustrating a side view of the actuating device of FIG. 2, according to various implementations of the invention.
Figure 3B:
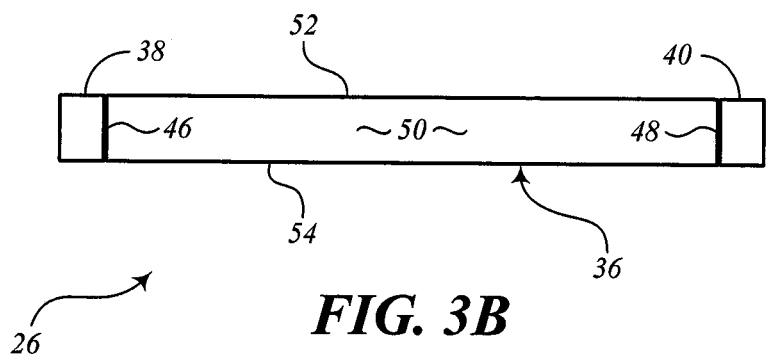
FIG. 3B is a diagram illustrating a top view of the actuating device of FIG. 2, according to various implementations of the invention.

FIGS. 3A and 3B are diagrams illustrating a side view and top view, respectively, of various implementations of actuating device 26 illustrated in FIG. 2. Actuating device 26 includes a reservoir 36, a first pressure actuator 38, and a second pressure actuator 40. As illustrated in the side view of FIG. 3A, reservoir 36 includes a top 42, bottom 44, and ends 46 and 48. As illustrated in the top view of FIG. 3B, reservoir 36 also includes a first side 52 and a second side 54. Reservoir 36 is liquid-tight and is configured to contain a liquid 50, such as water, oil, a magneto-rheological liquid, an electro-rheological liquid, or other liquid medium.

In some implementations, bottom 44, ends 46 and 48, and sides 52 and 54 may comprise a rigid material for supporting liquid 50 and for maintaining a fixed distance between first pressure actuator 38 and second pressure actuator 40. In these implementations, top 42 may be made of a flexible membrane, which is designed to deform according to the pressure wave patterns formed in or flowing through liquid 50. In some implementations, one or more of the top 42, bottom 44, and sides 52 and 54 may be formed from a flexible membrane or other flexible material, such as polyurethane, latex or similar material, in order to allow actuating device 26 to conform to any shape on which it is placed.

Actuating device 26 of FIG. 3 can be used in a number of different applications. For example, when used for providing socio-affective stimulus to a user, the flexible membrane, such as top 42, may be positioned against the user's skin or within clothing such that movement of flexible membrane 42 can be sensed by the user. In this way, actuating device 26 can provide low frequency waves to simulate the sensation of someone stroking the user's arm or tapping the user on the shoulder. In order to increase the size of the actuation area, actuation device 26 can be configured with a number of long reservoirs, each actuated by one or more pressure actuators. Also, reservoirs can also be arranged end to end, side by side, in an array, or in other configurations to fit certain sizes as needed.

As illustrated in FIG. 3, the channel in which liquid 50 is contained is substantially one dimensional, which allows for easy control of the waves. However, in other implementations, reservoir 36 can be given any shape, such as rectangular, triangular, circular, elliptical, etc. Processing device 12 can be programmed in a way that allows control over every portion of flexible membrane 42 to create a two-dimensional wave pattern. Also, one or more actuators may be arranged in fixed positions around the periphery of reservoir 36 to create various patterns of standing waves.

In some implementations, one or more pressure sensors can be arranged within or adjacent to the top 42, bottom 44, first side 52, and/or second side 54. These pressure sensors can be used to perform a closed loop control for the first pressure actuator 38 and/or second pressure actuator 40 by sensing the local pressure along the length of the reservoir 36 and providing an estimate of the actual standing wave pattern being displayed. This information can be fed back to control circuitry, such as drivers 22 and 24 (FIG. 2), which drives the pressure actuators 38 and 40. The feedback control circuitry can be used to accommodate for environmental perturbations such as acceleration of the device, pressures related to the parts of the user's body in contact with the flexible surfaces 42, 44, 52, and/or 54, etc.

In addition to standing waves, the pressure actuators 38 and 40 may be configured to create other types of static and/or dynamic pressure outputs. For example, other pressure output configurations, such as traveling waves and arbitrary static or moving patterns, can be created on the flexible surfaces.

Figure 4:
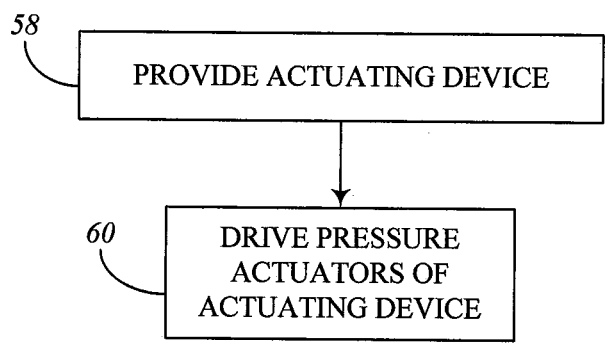
FIG. 4 is a flow diagram illustrating a method of creating a haptic pressure wave output, according to various implementations of the invention.

FIG. 4 is a flow diagram illustrating a method of creating a haptic pressure wave output, according to one embodiment. As indicated in block 58, an actuating device is provided. The actuating device may include, for example, a liquid-filled reservoir having at least one side that includes a flexible membrane. The actuating device may also include one or more pressure actuators positioned, for example, at the ends of the reservoir. Also, the actuating device may include one or more drive circuits to drive the respective pressure actuators.

As indicated in block 60 of FIG. 4, the pressure actuators of the actuating device are driven. For instance, the pressure actuators can be driven in such a way as to create interference effects, such as peaks, troughs, rippling effects, or other interference effects, along the length of the reservoir. The interference effects in turn cause the flexible membrane to deform in response to the waves. Thus, a user directly or indirectly in contact with the flexible membrane can tactilely sense the wave patterns. Particularly, the pressure actuators can be driven in a controlled manner to create various wave patterns, including but not limited to standing waves. The pressure actuators can also be driven by the drive circuits to create harmonics that can be used to better define the shapes of the waves at various points along the length of the reservoir.

It should be understood that the steps, processes, or operations described herein may represent any module or code sequence that can be implemented in software or firmware. In this regard, these modules and code sequences can include commands or instructions for executing specific logical steps, processes, or operations within physical components. It should further be understood that one or more of the steps, processes, and/or operations described herein may be executed substantially simultaneously or in a different order than explicitly described, as would be understood by one of ordinary skill in the art.

The embodiments described herein represent a number of possible implementations and examples and are not intended to necessarily limit the present disclosure to any specific embodiments. Instead, various modifications can be made to these embodiments as would be understood by one of ordinary skill in the art. Any such modifications are intended to be included within the spirit and scope of the present disclosure and protected by the following claims.

The invention claimed is:

1. A haptic output device comprising:
a liquid-tight reservoir filled with a liquid, at least one side of the reservoir including a flexible membrane;
a first actuator located outside of the reservoir and in physical contact with the reservoir and configured to transmit vibrations to the liquid to impart pressure waves to the liquid; and
a first driver configured to drive the first actuator,
wherein the first driver is configured to drive the first actuator such that a pressure wave from the first actuator and a reflected pressure wave from a portion of the reservoir at an opposite end from the first driver form a standing wave in the liquid, and
wherein the pressure waves interact with the flexible membrane to supply a haptic effect to a user.

2. The haptic output device of claim 1, wherein the first actuator is driven to create standing waves in the liquid, thereby forming a standing wave pattern with respect to the flexible membrane.

3. The haptic output device of claim 1, further comprising one or more sensors configured to sense the pressure waves.

4. The haptic output device of claim 3, wherein the one or more sensors are configured to control the first driver based on the sensed pressure waves.

5. The haptic output device of claim 1, wherein the liquid is water.

6. The haptic output device of claim 1, wherein the liquid is oil.

7. The haptic output device of claim 1, further comprising one or more electromagnetic field generators configured to control the pressure waves, wherein the liquid is a magneto-rheological liquid.

8. The haptic output device of claim 1, further comprising one or more electromagnetic field generators configured to control the pressure waves, wherein the liquid is an electro-rheological liquid.

9. The haptic output device of claim 1, wherein the pressure waves imparted on the liquid simulate socio-affective sensations.

10. The haptic output device of claim 9, wherein the haptic output device resides on a user's garment.

11. The haptic output device of claim 1, wherein the haptic output device resides on a mobile device.

12. The haptic output device of claim 1, wherein the haptic output device resides on a computer peripheral.

13. The haptic output device of claim 1, further comprising a second actuator in physical contact with the reservoir, the first actuator and second actuator being positioned a fixed distance apart from each other on opposite ends of the reservoir.

14. The haptic output device of claim 13, further comprising a second driver configured to drive the second actuator.

15. The haptic output device of claim 14, wherein the first driver and second driver are coordinated to create standing waves in the liquid.

16. The haptic output device of claim 15, wherein the standing waves created in the liquid form a standing wave pattern with respect to the flexible membrane.

17. The haptic output device of claim 13, wherein the first actuator and second actuator include piezoelectric actuators.

18. The haptic output device of claim 13, wherein the first actuator and second actuator include voice coils.

19. The haptic output device of claim 13, wherein the first actuator and second actuator are configured to have a frequency bandwidth from about 0 Hz to about 2 kHz.

20. The haptic output device of claim 13, further comprising one or more additional actuators arranged around a periphery of the reservoir.

21. A system comprising:
means for containing a liquid;
means for actuating opposing ends of the containing means; and
means for driving the actuating means to cause the actuating means to create pressure waves in the liquid, thereby providing haptic effects to a user, wherein the driving means is configured to cause the actuating means to produce pressure waves using frequency harmonics to create specific wave patterns.

22. The system of claim 21, wherein the actuating means is configured to create standing waves in the liquid.

23. The system of claim 21, wherein the actuating means comprises actuators selected from the group consisting of piezoelectric actuators and voice coil actuators.

24. The system of claim 21, wherein the actuating means is configured to produce haptic effects that can be interpreted as socio-affective sensations by the user.

25. A haptic output device comprising:
   a liquid-tight reservoir filled with a liquid, at least one side of the reservoir including a flexible membrane;
   a first actuator located outside of the reservoir and in physical contact with the reservoir and configured to transmit vibrations to the liquid to impart pressure waves to the liquid;
   a first driver configured to drive the first actuator;
   a second actuator in physical contact with the reservoir, the first actuator and second actuator being positioned a fixed distance apart from each other on opposite ends of the reservoir; and
   a second driver configured to drive the second actuator,
   wherein the first driver and second driver are coordinated to create standing waves in the liquid, and
   wherein the pressure waves interact with the flexible membrane to supply a haptic effect to a user.

26. The haptic output device according to claim 25, wherein the standing waves created in the liquid form a standing wave pattern with respect to the flexible membrane.

* * * * *